US010376671B2

(12) United States Patent
Byrnes et al.

(10) Patent No.: US 10,376,671 B2
(45) Date of Patent: *Aug. 13, 2019

(54) LUBRICIOUS EXTRUDED MEDICAL TUBING

(71) Applicant: Contech Medical, Inc., Providence, RI (US)

(72) Inventors: Raymond A. Byrnes, Coventry, RI (US); Christopher M. Byrnes, Coventry, RI (US); Frank E. Barrett, Warwick, RI (US)

(73) Assignee: Contech Medical, Inc., Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/670,905

(22) Filed: Aug. 7, 2017

(65) Prior Publication Data

US 2017/0333669 A1 Nov. 23, 2017

Related U.S. Application Data

(63) Continuation of application No. 13/722,704, filed on Dec. 20, 2012, now Pat. No. 9,744,332.
(Continued)

(51) Int. Cl.
*A61M 25/00* (2006.01)
*B29D 23/00* (2006.01)
(Continued)

(52) U.S. Cl.
CPC ......... *A61M 25/002* (2013.01); *A61L 29/041* (2013.01); *A61L 29/123* (2013.01);
(Continued)

(58) Field of Classification Search
CPC . C08L 83/04; C08L 2205/03; A61M 25/1029; A61M 2025/1031; A61M 25/10; A61M 2025/0024; A61M 2025/006; A61M 2025/0062; A61M 25/0009; A61M 25/0021; B29D 23/00; B29K 2083/00; B29K 2995/0046; Y10S 424/14; Y10S 514/841; A61L 29/126; A61L 29/123; A61L 29/041; A61L 2400/10;
(Continued)

(56) References Cited

U.S. PATENT DOCUMENTS 3,636,595 A 1/1972 Wines
4,280,500 A 7/1981 Ono
(Continued)

FOREIGN PATENT DOCUMENTS

WO WO 03/103746 A1 12/2003

*Primary Examiner* — Yan Lan
(74) *Attorney, Agent, or Firm* — Nixon Peabody LLP (57) ABSTRACT

A medical tube having improved lubricity is disclosed. The medical tube is produced by extruding a polymer material blended with a lubricity enhancing additive through a resilient die. The polymer material can be medical-grade high-density polyethylene, and the lubricity enhancing additive can be a silicone-based or alloy-based material. The medical tube can include one or more internal elongated protuberances so as to reduce the internal surface area of the medical tube available to generate friction on a guide wire inserted or withdrawn through the medical tube.

18 Claims, 7 Drawing Sheets

Related U.S. Application Data (60) Provisional application No. 61/656,302, filed on Jun. 6, 2012, provisional application No. 61/587,859, filed on Jan. 18, 2012.

(51) Int. Cl.
*B29C 47/00* (2006.01)
*A61L 29/04* (2006.01)
*A61L 29/12* (2006.01)
*B29C 48/10* (2019.01)
*B29K 83/00* (2006.01)

(52) U.S. Cl.
CPC ....... *A61L 29/126* (2013.01); *A61M 25/0009* (2013.01); *A61M 25/0021* (2013.01); *A61M 25/0023* (2013.01); *A61M 25/0045* (2013.01); *B29C 48/10* (2019.02); *B29D 23/00* (2013.01); *A61L 2400/10* (2013.01); *A61M 2025/006* (2013.01); *A61M 2025/0062* (2013.01); *B29K 2083/00* (2013.01); *B29K 2995/0046* (2013.01); *Y10T 428/139* (2015.01)

(58) Field of Classification Search
CPC ............... B29C 48/10; Y10T 428/1334; Y10T 428/139; Y10T 428/31663
USPC .................. 428/35.7, 36.9, 36.91, 327, 35.5; 623/1.13, 1.15, 1.11, 1.22, 1.49; 604/265
See application file for complete search history.

(56) References Cited

U.S. PATENT DOCUMENTS

| | | |
|---|---|---|
| 4,616,064 A | 10/1986 | Zukosky |
| 5,263,945 A | 11/1993 | Byrnes |
| 5,282,479 A | 2/1994 | Havran |
| 5,439,454 A | 8/1995 | Lo |
| 6,086,970 A | 7/2000 | Ren |
| 6,165,158 A | 12/2000 | Dutta |
| 6,277,093 B1 | 8/2001 | Lee |
| 6,405,414 B1 | 6/2002 | Byrnes |
| D459,977 S | 7/2002 | Byrne |
| 6,431,219 B1 | 8/2002 | Redler |
| 6,464,683 B1 | 10/2002 | Samuelson |
| 6,506,333 B1 | 1/2003 | Qin |
| 6,582,440 B1 | 6/2003 | Brumbach |
| 8,480,650 B2 | 7/2013 | Ehrenreich |
| 9,067,040 B2 * | 6/2015 | Byrnes .................. A61L 29/126 |
| 9,744,332 B2 * | 8/2017 | Byrnes .................. A61L 29/126 |
| 2003/0165647 A1 | 9/2003 | Kaneko |
| 2005/0124976 A1 | 6/2005 | Devens, Jr. |
| 2006/0171971 A1 | 8/2006 | Marsh |
| 2007/0215268 A1 | 9/2007 | Pingleton |
| 2008/0257441 A1 | 10/2008 | Allen |
| 2010/0268192 A1 | 10/2010 | El-Hibri |
| 2015/0038923 A1 | 2/2015 | Byrnes |

\* cited by examiner

LUBRICIOUS EXTRUDED MEDICAL TUBING

CROSS-REFERENCE TO RELATED APPLICATION

This application is a continuation of prior application Ser. No. 13/722,704, filed Dec. 20, 2012, now allowed, which claims the benefit of U.S. Provisional Application Nos. 61/656,302, filed Jun. 6, 2012, and 61/587,859, filed Jan. 18, 2012, each of which is hereby incorporated by reference herein in its entirety.

FIELD OF INVENTION

The present invention generally relates to extruded tubing useful for medical applications, such as protective dispenser coils for medical catheters or medical guide wires. More specifically, the present invention is directed to an extruded medical tubing formed from a blended thermoplastic material with an interior surface having enhanced lubricity to allow for efficient insertion and withdrawal of medical devices such as guide wires and/or catheters.

BACKGROUND

Medical tubing is used to house surgical medical devices during shipping and handling. Such medical tubing may be referred to as a protective dispenser tubing. Examples of medical devices distributed in protective dispenser tubing include guide wires and catheters for cardiovascular surgical interventions. The dispenser tubing is desirably coiled to allow for efficient packaging and handling. The dispenser tubing is generally packaged so as to maintain sterility of the medical devices situated within the tubing as well as prevent any damage or marring to sensitive instrumentation, such as delivery devices for cardiovascular surgery, e.g., stents, balloons, etc. Prior to shipment, such dispenser tubing is loaded with the medical devices in a sterile environment. During a surgical procedure, the medical devices are withdrawn from the dispenser tubing just prior to insertion into a patient's vascular system by medical personnel.

Protective dispenser tubing is generally formed by extruding an organic resin, such as polyethylene, polyolefin, polypropylene, etc, through a die. The temperature and/or pressure applied to the material is controlled to achieve a desired viscosity to allow for the material to be extruded through the die while achieving results that satisfy desired tolerances. Once the material is extruded through the die to take a tubular shape, the resulting tubing is allowed to cool and cut to desired lengths.

The dispenser tubing is desirably formed from a material exhibiting sufficient resistance to crushing forces to substantially maintain the dimensions of an internal passageway of the tubing under ordinary external forces encountered during shipping and handling. The tubing also desirably exhibits sufficient flexibility to allow the tubing to be coiled and thereby allow for more compact and efficient packaging of the medical devices housed within. Systems and devices for retaining dispenser tubing in a coiled configuration during shipping and handling operations is described, for example, by U.S. Pat. No. 6,405,414, the contents of which are incorporated entirely herein by reference.

Some applications of guide wires, stents, and other vascular medical devices housed within dispenser tubing, to provide cardiovascular interventions during a surgical procedure are described in U.S. Pat. No. 6,464,683, the contents of which are incorporated entirely herein by reference. In some applications, the medical device is introduced into the patient's vascular system by an introducing catheter "introducer" incorporating a cannula to puncture the patient's skin, at which point the guide wire, catheter, or other medical device can be directed, e.g., pushed, to the desired treatment region within the patient's vascular system. An example of a guide wire introducer is described U.S. Pat. No. 5,282,479, the contents of which are incorporated entirely herein by reference.

SUMMARY

Dispenser tubing is regularly loaded with medical devices, such as guide wires, and then the medical device is extracted by a medical professional during a surgical treatment using the medical device. Some guide wires can be as long as 180 inches, and loading such a lengthy guide wire can result in snags, stoppages, and kinks in the guide wire. In addition to the potential for damaging the guide wire, such a cumbersome loading procedure is costly and unmanageable in a large operation. There is therefore a need for a dispenser tube with enhanced lubricity along its internal surface such that medical devices, such as guide wires can be readily loaded and unloaded without problems typical of conventional dispenser tubes.

The magnitude of the motion-opposing frictional forces generated between the dispenser tube and a guide wire housed therein is proportional to, among other things, the coefficient of friction between the contacting surfaces of the two and the cumulative area the guide wire contacts any portion of the dispenser tube. The present disclosure provides at least two methods for improving the lubricity of a dispenser tube, which can be employed separately, or together to benefit from a combined effect. By providing elongated protuberances along an internal surface of a dispenser tube, the cumulative contact area between the guide wire and the dispenser tube is reduced, relative to a dispenser tube with a smooth, non-striated interior surface. Thus, the amount of motion-opposing friction between the guide wire and the striated dispenser tube is reduced by reason of the reduced contact area. Additionally or alternatively, the polymer matrix forming the extruded dispenser tube can be blended with a lubricity enhanced additive, such as an alloy-based or silicon-based additive. As described herein, the lubricity enhanced additive reduces the coefficient of friction of the internal surface of the dispenser tube and thereby reduces friction forces between a dispenser tube so formed and a guide wire.

Some embodiments of the present disclosure provide dispenser tubing extruded from a poly/alloy or poly/silicone blended material mixed according to the present disclosure and having a smooth (i.e., non-striated) interior surface. Some embodiments of the present disclosure provide dispenser tubing extruded from a thermoplastic material, such as medical grade high density polyethylene and having a striated interior surface. Some embodiments of the present disclosure provide dispenser tubing extruded from a poly/alloy or poly/silicone blended material mixed according to the present disclosure and having a striated interior surface.

Some embodiments of the present disclosure include a lubricous medical tube formed from a blended material including organic polymer resin, and a lubricity enhancing additive blended with the organic polymer resin to form a blended material. The blended material can be disposed in a substantially tubular configuration bounded by an inner surface and an outer surface encompassing the inner surface.

In some embodiments, the organic polymer resin can include medical-grade high-density polyethylene. In some embodiments, the lubricity enhancing additive is selected from a silicon-based material or an alloy-based material. In some embodiments, the lubricity enhancing additive can include Franklinite. In some embodiments, the lubricity enhancing additive is blended with the organic polymer resin at a concentration of less than 10%, or of less than 5%, or of approximately 3%, or of approximately 2%, or of approximately 1%.

Some embodiments of the present disclosure provide for the inner surface of the medical tube to be formed with a plurality of elongated protuberances arranged to extend substantially parallel to a length dimension of the medical tube. In some embodiments, the plurality of elongated protuberances are configured such that each of the protuberances is characterized by a raised apex, the raised apex being closer to an axis of substantial cylindrical symmetry of the medical tube than a depressed region located between adjacent ones of the plurality of elongated protuberances. In some embodiments, the plurality of elongated protuberances are configured such that a medical guide wire inserted in the medical tube contacts at least a portion of one or more of the plurality of elongated protuberances, including the raised apexes, without contacting at least a portion of the inner surface between adjacent ones of the plurality of protuberances. In some embodiments, the plurality of elongated protuberances are substantially evenly spaced about the interior surface of the medical tube. In some embodiments, the inner surface is sufficiently lubricious to allow insertion or withdrawal of a guide wire into the lubricious medical tube while the lubricious medical tube remains in a coiled configuration.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
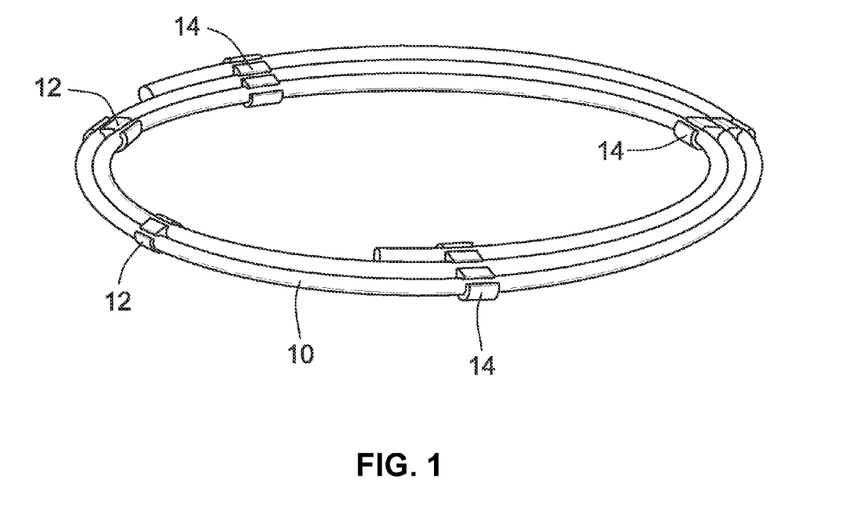
FIG. 1 shows a lubricious dispenser tube for housing a medical device such as a guide wire or a catheter.

FIG. 1 shows a lubricious dispenser tube 10 for housing a medical device such as a guide wire or a catheter. For expediency in the remainder of this disclosure, unless specifically stated otherwise, the various lubricious dispenser tubes disclosed herein will be described with reference to housing a guide wire. However, it is specifically noted that the dispenser tubes described herein can also house catheters and other medical devices suitable for being dispensed from a sterile coiled tube to maintain sterility and integrity of the medical device during transport. The lubricious dispenser tube 10 is securely held in a coiled position by the clips 12, 14. The clips can be extruded unitary plastic clips having a plurality of adjacent sockets for griping the tube 10 and securing it to another portion of the tube 10 so as to coil the dispensing tube 10 in a spiral configuration. The clips can have, for example, two sockets (12) or three sockets (14). An example of a suitable clip for securing a dispensing tube in a spiral wound configuration is described in U.S. Pat. No. 6,405,414, the contents of which are incorporated herein in its entirety. Thus, a guide wire housed within the dispenser tube 10 can be compactly and efficiently handled to be delivered from a sterile production and packaging environment to a surgical suite or operating room without sacrificing the structural integrity or sterility of the guide wire housed.

Figure 2A:
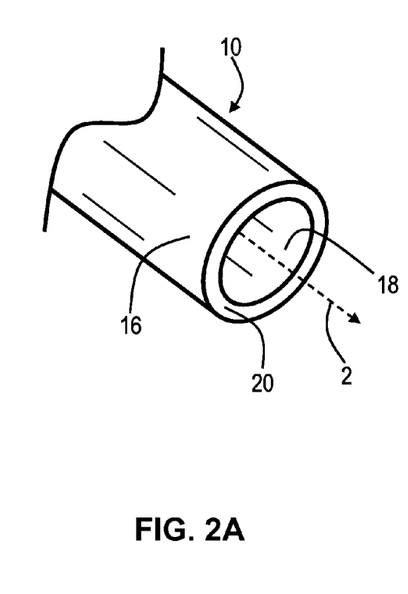
FIG. 2A is an aspect view of the dispenser tube showing an end of the dispenser tube in an open state, i.e., with no guide wire housed within the dispenser tube.

FIG. 2A is an aspect view of the dispenser tube 10 showing an end 20 of the dispenser tube 10 in an open state, i.e., with no guide wire housed within the dispenser tube 10. The dispenser tube 10 has an exterior cylindrical ("tubular") surface 16 and an interior cylindrical surface 18. The exterior surface 16 is substantially equidistant from a central axis 2 defining an axis of substantial cylindrical symmetry of the dispenser tube 10. The interior surface 18 is located radially interior to the exterior surface 16, with respect to the central axis 2, and is also substantially equidistant from the central axis 2. The dispenser tube 10 can be formed by an extrusion process to extrude material between two surfaces of a die corresponding to the interior and exterior surfaces 16, 18 such that the extruded material is disposed between the interior and exterior surfaces 16, 18.

Figure 2B:
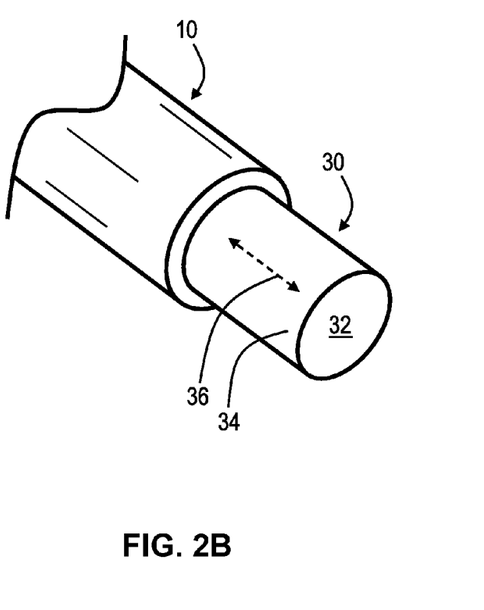
FIG. 2B is an aspect view of the dispenser tube 10 shown in FIG. 2A, where the dispenser tube is housing a guide wire.

The interior surface 18 defines a passageway, i.e., interior channel or lumen, of the dispenser tube for housing medical guide wires and for receiving guide wires as they are loaded (during packaging) and unloaded (in connection with a surgical procedure). As shown in FIG. 2B, a guide wire 30 is inserted and/or withdrawn from the dispenser tube 10. The guide wire 30 can be formed of materials including stainless steel, nitinol, or other materials used for guide wires in angioplasty, stent, and other cardiovascular surgical procedures. The guide wire 30 has an end 32 and an external side wall 34, which can be a substantially cylindrical wall sized to fit within the internal surface 18 of the dispenser tube 10 so as to allow the guide wire 30 to be housed within the dispenser tube 10. As indicated by the directional arrow 36, the guide wire 30 is inserted and withdrawn from the dispenser tube via longitudinal forces, e.g., pushing or pulling forces, exerted on the guide wire 30 with respect to the dispenser tube 10. During insertion or withdrawal of the guide wire 30 to or from the dispenser tube 10, the external side wall 34 contacts the interior surface 18 of the dispenser tube 10, which contact results in motion-opposing frictional forces between the interior surface 18 of the dispenser tube 10 and the external side wall 34 of the guide wire 30.

According to some embodiments of the present disclosure, the extruded material forming the dispenser tube 10 is a material that includes an organic resin as a matrix material and a lubricity enhancing additive blended with the resin. In some embodiments the resin can be a thermoplastic polymer-based material, such as medical grade high density polyethylene. Some embodiments can also incorporate polyolefin, polypropylene, and the like as a matrix material or blended ingredient. The lubricity enhancing additive can be a silicon-based material, such as siloxane and/or an ultra-high molecular weight silicone material. In some embodiments, the lubricity enhancing additive can additionally or alternatively include an alloy, such as Franklinite, $(Zn,Mn^{2+},Fe^{2+})(Fe^{3+},Mn^{3+})_2O_4$, or another alloy having particles with surface hardness greater than that of the surrounding poly matrix.

In some embodiments, the lubricity enhancing additive can additionally or alternatively include materials with a melt flow index (MFI) between approximately 7 and approximately 13 grams per 10 minutes, under the standards at ASTM D 1238 and/or ISO 1133. In some embodiments, the lubricity enhancing additive can additionally or alternatively include materials with a bulk density between approximately 30 and approximately 35 pounds per cubic foot, under the standards at ASTM D 1895-67(B). In some embodiments, the lubricity enhancing additive can additionally or alternatively include materials with a moisture content less than approximately 0.5% as determined by an electronic moisture analyser, for example. Thus, the lubricity enhancing additive can have a molecular structure, molecular weight, and/or grain size, etc. such that the additive material has an MFI between approximately 7 and approximately 13 gms/10 mins; a bulk density between approximately 30 and approximately 35 lbs/ft$^3$; and/or a moisture content less than approximately 0.5%. In some examples, the lubricity enhancing additive can be a polymeric material, alloy-based material, and/or silicone material that is suitable for food and/or medical applications, such as additives sanctioned by the F.D.A. for use under conditions subject to contact with food and/or medical materials. Additionally or alternatively, the lubricity enhancing additive (and the resulting polymeric blended material) can be substantially thermally stable at extrusion processing temperatures, such as, for example, temperatures between approximately 350 degrees and approximately 450 degrees. Furthermore, the lubricity enhancing additive can be a combination of an alloy-based material (such as a material including Franklinite) and a polymeric material (such as a material with the properties described above).

In some embodiments, the lubricity enhancing additive, such as the alloy, is not readily soluble within the melted polymer matrix blend and as a result migrates preferentially toward the tube surfaces during the extrusion. Such an extruded dispenser tube can be at least partially surrounded by a film or thin layer of an enhanced amount of lubricity enhancing additive. The lubricity enhancing additive, such as, for example, an alloy material, a polymeric material, a silicone material, or a combination of such materials, is blended with the matrix material at a concentration in the range of 0.5% to 10%. In some embodiments the lubricity enhancing additive can be blended with the matrix material at a concentration of approximately 2%. In some embodiments the lubricity enhancing additive can be blended with the matrix material at a concentration of approximately 3%. In some other examples, the lubricity enhancing additive can optionally be blended with the matrix at a concentration in the range of 25.8%±2%.

The resulting blended material is heated so as to provide a desired viscosity and/or solubility sufficient for extrusion processing and the blended material (e.g., the poly/alloy blended material) is directed through a die to form the dispenser tube 10 described above in connection with FIGS. 1-2. As a result of the presence of the blended silicone-based or alloy-based lubricity enhancing additive, the lubricious dispenser tube 10 exhibits a decreased coefficient of friction between the internal surface 18 of the dispenser tube 10 and the external side wall 34 of the guide wire 30. The enhanced lubricity may be due to the increased presence of hard surface particles, near the interior surface 18, which are relatively less likely than conventional polymer matrix material particles to microscopically deform or spread in response to microscopic physical contact from the guide wire 30, which microscopic deforming and/or spreading generates a motion-opposing frictional force.

The resulting lubricious dispenser tube 10 is less likely to grab, kink, or cause stoppage of the guide wire 30 within the dispenser tube 10 before fully inserted. Furthermore, by increasing the lubricity, i.e., decreasing the coefficient of friction of the interior surface 18, the guide wire 30 is loaded into the dispenser tube 10 with less resistance, and can be loaded while the dispenser tube 10 remains in a coiled ("spiral wound") configuration, such as the coiled configuration illustrated in FIG. 1. Even where it may have been possible to load the guide wire while the dispenser tube 10 was coiled, the dispenser tube 10 can now be coiled more tightly than previously possible while loading the guide wire 30. Additionally or alternatively, the dispenser tube 30 can be more tightly wound than previously thought possible prior to shipping, because the lubricious interior surface 18 allows the guide wire 30 to be withdrawn from a coiled dispenser tube 10 that is coiled more tightly (e.g., at a smaller radius) than previously thought possible. As a result, the lubricious dispenser tube 10 disclosed herein allows for more compact and efficient packaging of guide wires than previously available because the dispenser tube 10 can now be more tightly wound so as to take up a smaller area than previously thought possible.

Figure 3:
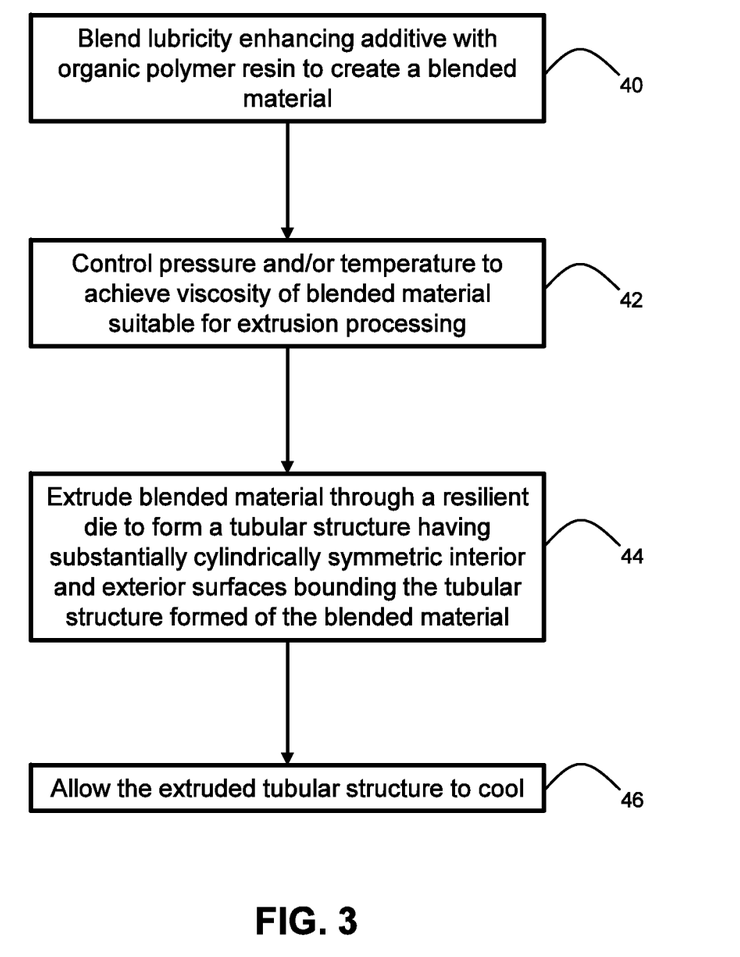
FIG. 3 is a flowchart illustrating an example procedure for preparing the lubricious dispenser tube shown and described in connection with FIGS. 1 and 2.

FIG. 3 is a flowchart illustrating an example procedure for preparing the lubricious dispenser tube 10 shown and described in connection with FIGS. 1 and 2. A lubricity enhancing additive is blended with an organic polymer resin (polymer matrix material) to create a blended material (40). The temperature and/or pressure of the blended material is controlled according to typical extrusion processing so as to achieve a viscosity of the blended material suitable for being extruded (42). The blended material is then extruded through a resilient die to form a tubular structure having substantially cylindrically symmetric interior and exterior surfaces bounding the tubular structure formed of the blended material (44). The extruded tubular structure is allowed to cool until it achieves a viscosity suitable for further processing, (46).

Further aspects of the present disclosure provide for enhancing the lubricity of dispenser tubing by providing a plurality of elongated raised protuberances along the interior surface of the tube. A guide wire inserted therein makes contact predominantly with the raised protuberances, rather than the entire interior surface and thereby avoids surface friction from at least some portions of the interior surface that are not raised.

Figure 4A:
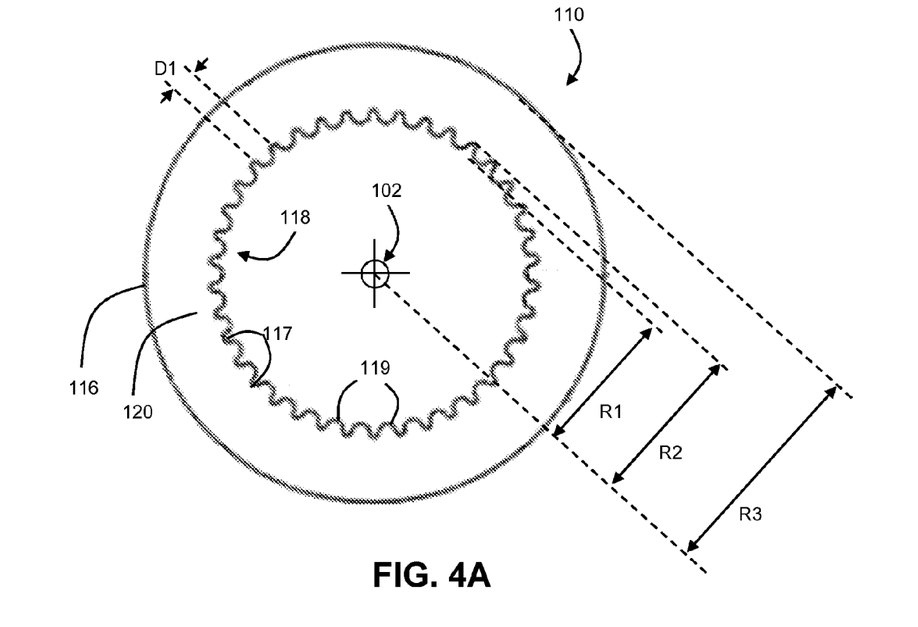
FIG. 4A is a cross-sectional view of a striated dispenser tube having a plurality of raised protuberances 119 along an internal surface of the dispenser tube.
Figure 4B:
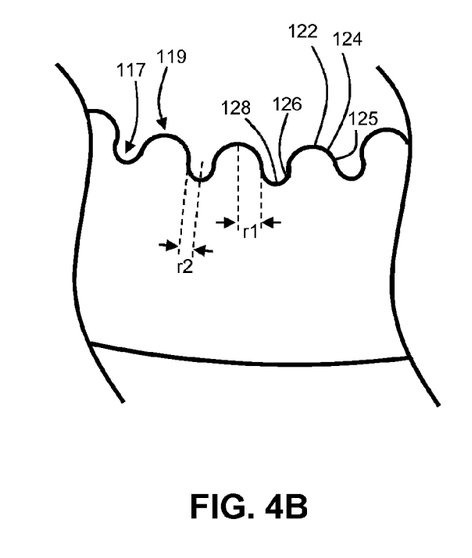
FIG. 4B provides a magnified view of a bottom portion of the cross-sectional view shown in FIG. 4A.

FIG. 4A is a cross-sectional view of a striated dispenser tube 110 having a plurality of raised protuberances 119 along an internal surface 118 of the dispenser tube 110. FIG. 4B provides a magnified view of a bottom portion of the cross-sectional view shown in FIG. 4A. The cross-sectional view in FIGS. 4A and 4B is taken along a plane substantially perpendicular to the imaginary axis 102 extending through the center of the striated dispenser tube 110. The plurality of raised protuberances 119 may be referred to alternatively as internal ribs, ridges, striations, etc. The raised protuberances generally extend along a direction substantially parallel to the imaginary axis 102.

It is specifically noted that in FIGS. 4A and 4B, there are a plurality of circumferentially evenly spaced protuberances 119, but only one or two such protuberances are explicitly labelled for ease of illustration. Similarly, between each of the plurality of protuberances 119, there exists a plurality of elongated depressions 117, which not each separately labelled in the drawings for each of illustration. It is also noted that the striated dispenser tube 110 is generally considered to be substantially cylindrically symmetric about the imaginary axis 102, with the interior surface 118, which is situated generally between a first radius R1 and a second radius R2 from the imaginary axis 102. By comparison, the exterior surface 116 of the striated dispenser tube 110 is substantially equidistant from the imaginary axis 102 at a distance R3, (e.g., the exterior surface 116 is substantially cylindrically symmetric with respect to the imaginary axis 102).

Each of the raised protuberances 119 can be generally circumferentially evenly spaced about the interior surface 118, and can be situated with adjacent protuberances 119 separated by depressions 117. An exemplary geometric arrangement of the protuberances 119 and the depressions 117 is described in connection with the close-in view in FIG. 4B. Generally, the depressions 117 include at least a portion of the interior wall 118 that is distant from the imaginary axis 102 by the second radius R2, and the protuberances 119 include at least a portion that is distant from the imaginary axis 102 by the first radius R1. Adjacent ones of the protuberances are separated by a distance D1, along the circumference of the interior surface. To name one example, the separation distance D1 can be 0.0088 inches, but the separation distance can be other numbers as well. The value of the first radius R1 is generally selected to allow passage of the guide wire 30 being housed within the striated dispenser tubing 110. The dimension of the second radius R2 is selected such that the difference between the first and second radii, which defines the maximal height of the protuberance 119 with respect to the depressions 117 is not substantially different from the separation distance between adjacent protuberances. For example, the value of R2 can be selected according to a formula, such as, e.g., R2−R1<k D1, wherein k is a small number, such as a number less than 5 or less than 3. If the height of the protrusion, i.e., R2−R1, is allowed to substantially exceed the separation distance, the protrusions become substantially taller than they are wide, and there is some risk that they may sacrifice structural integrity, for example, the protrusions 119 may wobble or otherwise be undesirably displaceable in response to a guide wire being loaded into the striated dispenser tube 110. In addition, the second radius R2 is selected to maintain a sufficient thickness of the wall 120, characterized generally by the difference between the third and second radii, i.e., R3−R2.

In addition, the number of protrusions 119 circumferentially located about the interior surface 118 can be adjusted for different sizes of the striated dispenser tube 118. In one example, a relationship may be established between one or more of the first radius (i.e., radius of the guide wire to be loaded), the second radius, and the separation distance D1. Such a relationship may desirably ensure that there remain a sufficient number of protrusions to allow the guide wire 30 to be loaded within the striated dispenser tubing by having the external side wall 34 of the guide wire 30 slide on portions adjacent ones of the plurality of protuberances 119 without contacting the depressions 117 between the protuberances 119.

To further illustrate the geometric arrangement of the protrusions 119 and the depressions 117, the dimensions of an example one of the protuberances 119 are described in connection with the enhanced view shown in FIG. 4B. The protuberance 119 is characterized by an apex 122 which appears in the cross section as the point on the protuberance 119 nearest the imaginary axis 102. For example, the apex 122 can be separated from the imaginary axis 102 by the first radius R1. Accordingly, the apexes 122 of the plurality of protuberances 119 define lines on the interior surface 118 that are most proximate to the imaginary axis 102. The apex 122 can be the crest of a pronounced region 124 having a curvature generally away from the imaginary axis 102. For example, the pronounced region 124 can be characterized by a radius of curvature with an axis internal to the wall 120 of the striated dispenser tube 110. The radius of curvature of the pronounced region can be the radius r1 illustrated in FIG. 4B. The pronounced region 124 continues to an inflection point 125, which is disposed on both sides of the pronounced region 124 at positions approximately equidistant from the apex 122. Upon crossing the inflection point 125, travelling from the pronounced region 124, the depressed region 126 is encountered. Thus, the inflection point 125 indicates a location of change of curvature. The depressed region 126 is characterized by the interior wall 118 curving generally toward the imaginary axis 102. For example, the depressed region 126 can be characterized by a radius of curvature with an axis inside the cavity defined by the interior surface 118 (e.g., not within the wall 120, but rather between the interior surface 118 and the imaginary axis 102). The radius of curvature of the depressed region 126 can be the radius r2 illustrated in FIG. 4B. The depressed region 126 includes a low point 128, which is the most distant point from the imaginary axis 102 within the depressed region 126, e.g., the distance given by the second radius R2.

Figure 4C:
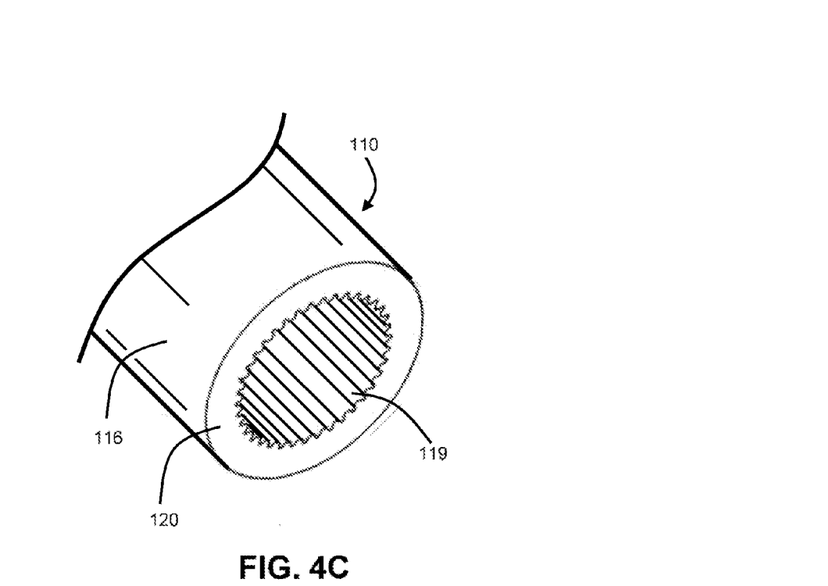
FIG. 4C is an aspect view of the striated dispenser tube showing an open end of the striated dispenser tube with the elongated protrusions visible on the interior surface.

FIG. 4C is an aspect view of the striated dispenser tube 110 showing an open end of the striated dispenser tube 110 with the elongated protrusions 119 visible on the interior surface 118. The striations are oriented substantially perpendicularly to the imaginary axis 102.

Figure 5A:
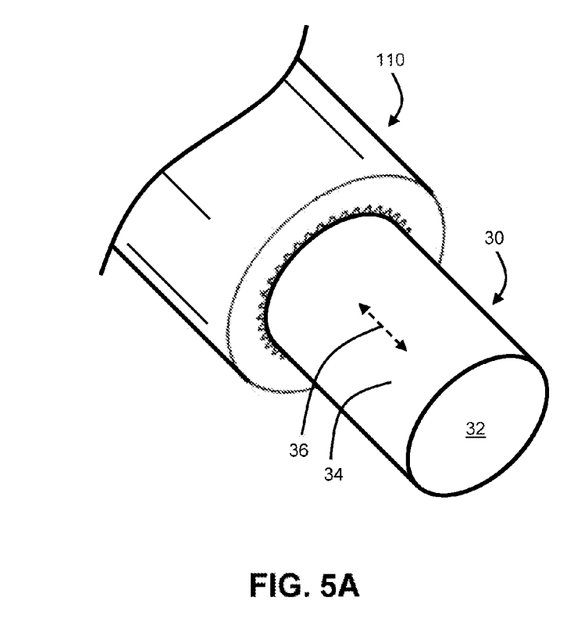
FIG. 5A is an aspect view of the striated dispenser tube similar to FIG. 4C, but where the striated dispenser tube is housing the guide wire.
Figure 5B:
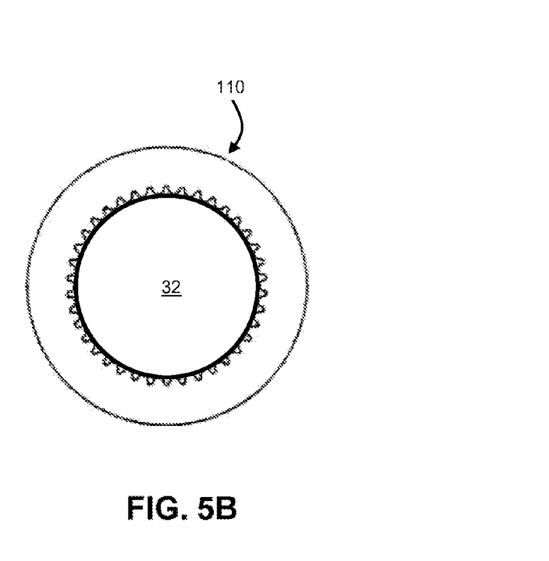
FIG. 5B illustrates a cross-sectional view of the striated dispenser tube housing the guide wire shown in FIG. 5A.

FIG. 5A is an aspect view of the striated dispenser tube 110 similar to FIG. 4C, but where the striated dispenser tube 110 is housing the guide wire 30. Similar to FIG. 2B, the directional arrow 36 illustrates the direction of insertion and/or withdrawal of the guide wire 30 with respect to the striated dispenser tube 110. FIG. 5B illustrates a cross-sectional view of the striated dispenser tube 110 housing the guide wire 30 shown in FIG. 5A.

As shown in FIGS. 5A and 5B, the guide wire 30 does not maintain a continuous circumferential connection to the interior surface 118 of the striated dispenser tube 110. Rather, the guide wire 30 slides along raised portions (e.g., portions including the apexes 122) of the elongated protuberances 119 without contacting the at least a portion of the interior surface 118 between adjacent ones of the elongated protuberances 119 (e.g., portions including the low points 128). Thus, the external side wall 34 of the guide wire 30 contacts only a portion of the interior surface 118 while being loaded or withdrawn from the striated dispenser tube 110.

Figure 6A:
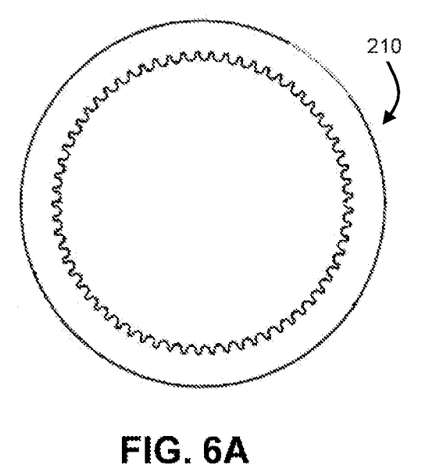
FIG. 6A is a cross-sectional view of an example of a striated dispenser tube having 65 circumferentially arranged elongated protuberances.

FIG. 6A is a cross-sectional view of an example of a striated dispenser tube 210 having 65 circumferentially arranged elongated protuberances. The individual elongated protuberances are similar to those described in connection with the striated dispenser tube 110 of FIGS. 4 through 5, but there are more such protuberances. In one example implementation of the striated dispenser tube 210, the circumferential distance between adjacent protuberances is 0.0088 inches, the outer diameter is 0.225 inches and the inner diameter is 0.175 inches.

Figure 6B:
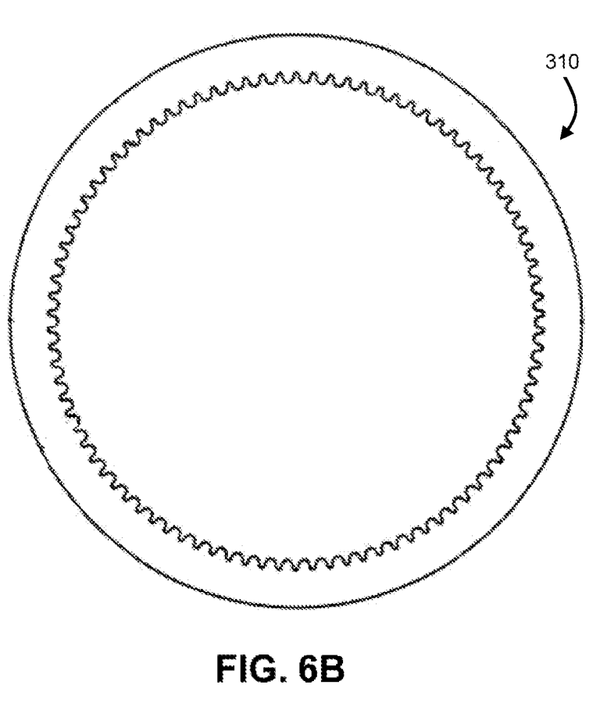
FIG. 6B is a cross-sectional view of an example of a striated dispenser tube having 90 circumferentially arranged elongated protuberances.

FIG. 6B is a cross-sectional view of an example of a striated dispenser tube 310 having 90 circumferentially arranged elongated protuberances. In one example implementation of the striated dispenser tube 310, the circumferential distance between adjacent protuberances is 0.0088 inches, the outer diameter is 0.300 inches and the inner diameter is 0.250 inches.

Exemplary dimensional values of dispenser tubes produced according to the present disclosure are provided below in Table 1.

TABLE 1

Exemplary dimensional values of lubricious extruded dispenser tubes according to embodiments of the present disclosure.

| Outer Diameter (2 R3) [inches] | Inner Diameter (2 R1) [inches] | Circumferential Distance Between Adjacent Protuberances [inches] | Number of Protuberances About the Circumference |
|---|---|---|---|
| 0.152 | 0.100 | 0.0088 | 28 ± 2 |
| 0.225 | 0.175 | 0.0088 | 65 ± 2 |
| 0.225 | 0.185 | 0.0088 | 68 ± 2 |
| 0.300 | 0.250 | 0.0088 | 90 ± 2 |

Figure 7:
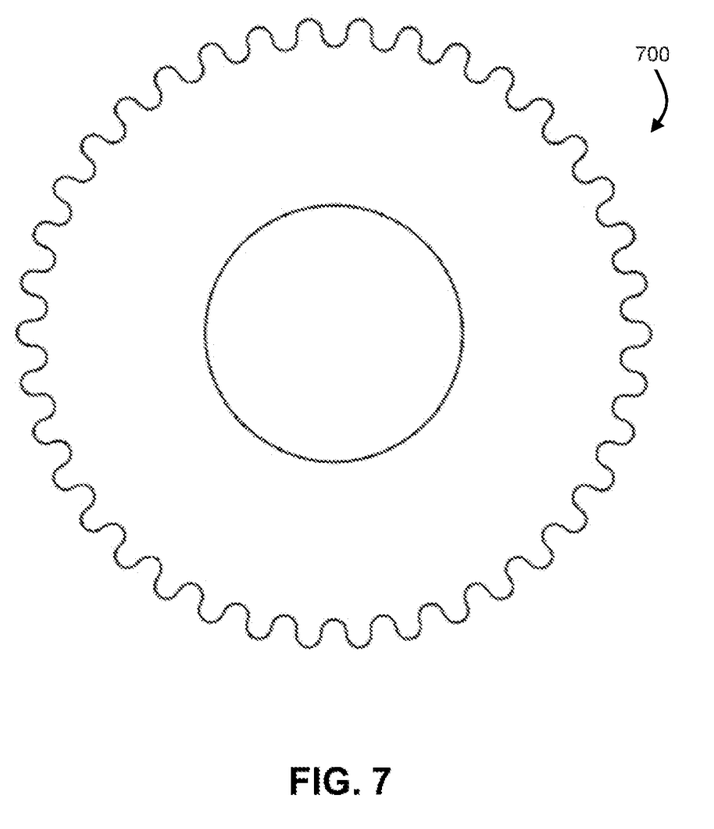
FIG. 7 is a top view of an extrusion die used to produce a striated dispenser tube in accordance with the present disclosure.

FIG. 7 is a top view of an extrusion die 700 used to produce a striated dispenser tube in accordance with the present disclosure. The extrusion die is constructed from a resilient material such as conventionally used in extrusion processing. The extrusion die can be constructed to be resilient to aspects encountered during extrusion processing, such as solvents, coolants, high pressure, high temperatures, etc. As shown in FIG. 7, the extrusion die 700 includes a removed central region and has a generally circular shape. The circumference of the extrusion die is surrounded by protruding ribs separated by intended spaces, which combine to define a striated interior surface of a dispenser tubing extruded via the extrusion die 700. The protruding ribs are generally terminated by a rounded feature. The protruding ribs are rounded with a radius of curvature having an axis interior to the extrusion die. Adjacent ones of the protruding ribs are separated by indented spaces that are also rounded, but with a radius of curvature having an axis external the extrusion die. As will be understood, during an extrusion process using the extrusion die 700, extruded material along and through the indented spaces between the protruding ribs become raised ridges, such as the elongated protuberances 119 described in connection with the striated dispenser tube 110 of FIGS. 4 and 5. Similarly, material extruded along the protruding ribs become intended valleys, between the raised ridges, such as the depressions 117 described in connection with the striated dispenser tube 110 of FIGS. 4 and 5.

Figure 8:
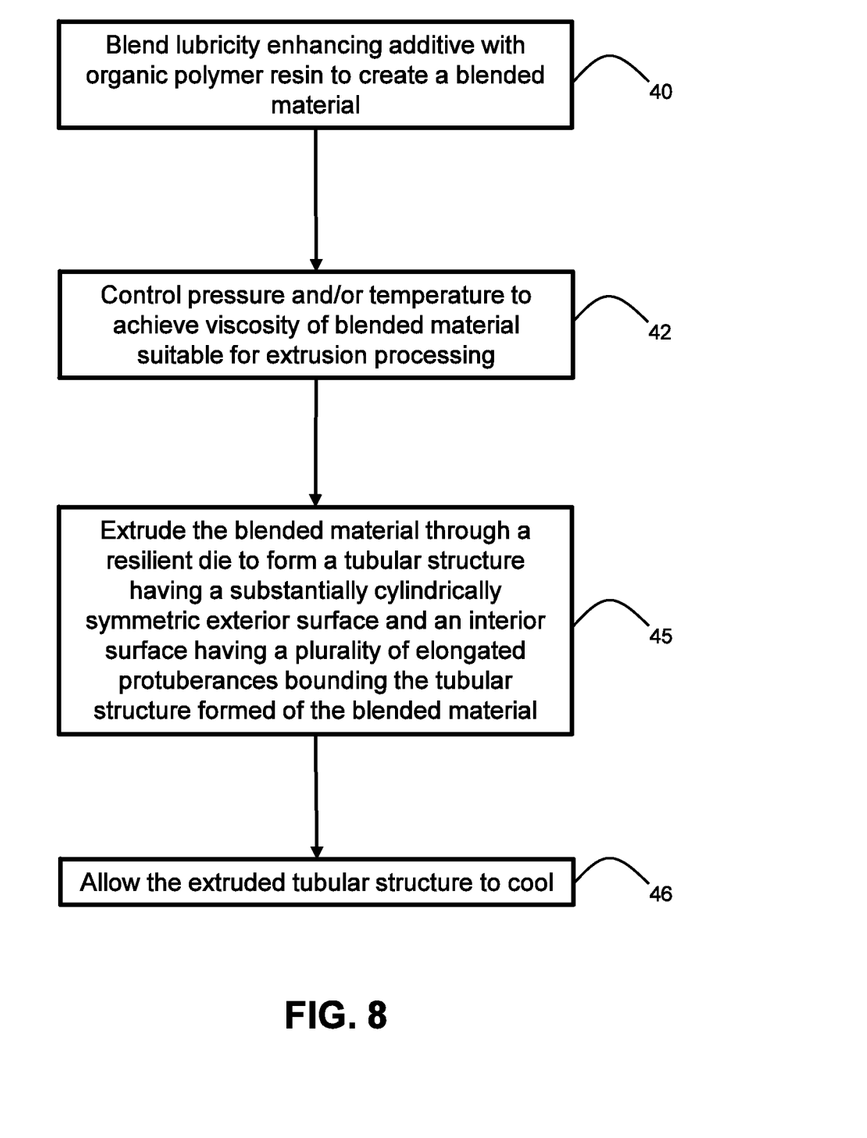
FIG. 8 is a flowchart illustrating an example procedure for preparing the lubricious dispenser tube shown and described in connection with FIGS. 4 through 5.

FIG. 8 is a flowchart illustrating an example procedure for preparing the lubricious dispenser tube 110 shown and described in connection with FIGS. 4 through 5 (or the lubricious dispenser tubes 210, 310 described in connection with FIGS. 6A and 6B). A lubricity enhancing additive is blended with an organic polymer resin (polymer matrix material) to create a blended material (40). The temperature and/or pressure of the blended material is controlled according to typical extrusion processing so as to achieve a viscosity of the blended material suitable for being extruded (42). The blended material is then extruded through a resilient die to form a tubular structure having a substantially cylindrically symmetric exterior surface and an interior surface having a plurality of elongated protuberances bounding the tubular structure formed of the blended material (45). The extruded tubular structure is allowed to cool until it achieves a viscosity suitable for further processing, (46).

The magnitude of the motion-opposing frictional forces generated between the striated dispenser tube 110 and the guide wire 30 is proportional to, among other things, the coefficient of friction between the contacting surfaces and the cumulative area where the external side wall 34 of the guide wire 30 contacts any portion of the interior surface 110. Accordingly, by providing the disclosed elongated protuberances 119 to thereby reduce the contact area between the guide wire 30 and the striated dispenser tube 110, relative to a dispenser tube with a smooth, non-striated interior surface, the amount of motion-opposing friction between the guide wire 30 and the striated dispenser tube 110 is reduced. Additionally or alternatively, the polymer matrix blended with a lubricity enhancing additive, such as an alloy-based or silicon-based additive, provides a reduced coefficient of friction between a dispenser tube 10, 110, 210, 310 formed from the blended material and the guide wire 30.

Some embodiments of the present disclosure provide dispenser tubing extruded from a poly/alloy or poly/silicone blended material mixed according to the present disclosure and having a smooth (i.e., non-striated) interior surface. Some embodiments of the present disclosure provide dispenser tubing extruded from a thermoplastic material, such as medical grade high density polyethylene and having a striated interior surface. Some embodiments of the present disclosure provide dispenser tubing extruded from a poly/alloy or poly/silicone blended material mixed according to the present disclosure and having a striated interior surface.

While there has been shown and described in some embodiments of a nebulizer assembly in accordance with the invention, it will be appreciated that many changes and modifications can be made therein without, however, departing from the essential spirit thereof. Thus, the invention is not limited to the particular embodiments disclosed herein, for it can be realized that various size and/or shapes of the tubular housing and/or nebulizer can be used for the purposes of the invention. The terminology used herein is for the purpose of describing particular embodiments only, and is not intended to limit the scope of the present invention, which is defined solely by the claims.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All numbers expressing quantities used herein should be understood as modified in all instances by the term "about." The term "about" when used in connection with percentages may mean±1%.

In the claims, as well as in the specification above, all transitional phrases such as "comprising," "including," "having," and "containing," are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

ALTERNATIVE IMPLEMENTATIONS

Alternative Implementation 1

A lubricous medical tube formed from a blended material including: organic polymer resin, and a lubricity enhancing additive blended with the organic polymer resin to form a blended material; and wherein the blended material is disposed in a substantially tubular configuration bounded by an inner surface and an outer surface encompassing the inner surface.

Alternative Implementation 2

The lubricious medical tube of alternative implementation 1, wherein the organic polymer resin includes medical grade high-density polyethylene.

Alternative Implementation 3

The lubricious medical tube of alternative implementation 1 to 2, wherein the lubricity enhancing additive is selected from a silicon-based material or an alloy-based material.

Alternative Implementation 4

The lubricious medical tube of any one of alternative implementations 1 to 3, wherein the lubricity enhancing additive includes Franklinite.

Alternative Implementation 5

The lubricious medical tube of any one of alternative implementations 1 to 4, wherein the lubricity enhancing additive is blended with the organic polymer resin at a concentration of less than 10%.

Alternative Implementation 6

The lubricious medical tube of any one of alternative implementations 1 to 5 wherein the lubricity enhancing additive is blended with the organic polymer resin at a concentration of less than 5%.

Alternative Implementation 7

The lubricious medical tube of any one of alternative implementations 1 to 6, wherein the lubricity enhancing additive is blended with the organic polymer resin at a concentration of approximately 3%.

Alternative Implementation 8

The lubricious medical tube of any one of alternative implementations 1 to 6, wherein the lubricity enhancing additive is blended with the organic polymer resin at a concentration of approximately 2%.

Alternative Implementation 9

The lubricious medical tube of any one of alternative implementations 1 to 6, wherein the lubricity enhancing additive is blended with the organic polymer resin at a concentration of approximately 1%.

Alternative Implementation 10

The lubricious medical tube of any one of alternative implementations 1 to 9, wherein the inner surface of the medical tube is formed with a plurality of elongated protuberances arranged to extend substantially parallel to a length dimension of the medical tube.

Alternative Implementation 11

The lubricious medical tube of alternative implementation 10, wherein the plurality of elongated protuberances are configured such that each of the protuberances is characterized by a raised apex, the raised apex being closer to an axis of substantial cylindrical symmetry of the medical tube than a depressed region located between adjacent ones of the plurality of elongated protuberances.

Alternative Implementation 12

The lubricious medical tube of alternative implementation 10 or 11, wherein the plurality of elongated protuberances are configured such that a medical guide wire inserted in the medical tube contacts at least a portion of one or more of the plurality of elongated protuberances, including the raised apexes, without contacting at least a portion of the inner surface between adjacent ones of the plurality of protuberances.

Alternative Implementation 13

The lubricious medical tube of any one of alternative implementations 10 to 12, wherein the plurality of elongated protuberances are substantially evenly spaced about the interior surface of the medical tube.

Alternative Implementation 14

The lubricious medical tube of any one of alternative implementations 1 to 13, wherein the inner surface is sufficiently lubricious to allow insertion or withdrawal of a guide wire into the lubricious medical tube while the lubricious medical tube is held in a coiled configuration.

Alternative Implementation 15

A method of preparing a medical tube comprising: blending an organic polymer resin with a lubricity enhancing additive to create a blended material; controlling the temperature or pressure of the blended material so as to achieve a viscosity of the blended material suitable for being extruded; extruding the blended material through a resilient die to form a tubular structure suitable for use as a dispenser tube for a medical device housed therein; and allowing the extruded tubular structure to cool until it achieves a state suitable for further processing.

Alternative Implementation 16

The method of alternative implementation 15, wherein the extruding is carried out to create an extruded a tubular structure having a substantially cylindrically symmetric exterior surface and an interior surface having a plurality of elongated protuberances bounding the tubular structure formed of the blended material.

Alternative Implementation 17

The method of alternative implementation 15 or 16, wherein the method is carried out so as to produce the medical tube disclosed in any one of alternative implementations 1 to 14.

Alternative Implementation 18

A dispenser assembly comprising: a lubricious medical tube formed from a mixture of an organic polymer resin blended with a lubricity enhancing additive, the lubricious medical tube configured such that the blended mixture is bounded between an inner surface and an external surface encompassing the inner surface, and a medical device housed within the lubricious medical tube.

Alternative Implementation 19

The dispenser assembly of alternative implementation 18, wherein the lubricious medical tube is a lubricious medical tube as disclosed in any one of alternative implementations 1 to 14.

Alternative Implementation 20

The dispenser assembly of alternative implementation 18 or 19, further comprising one or more tubing clips to secure the lubricious medical tube in a coiled configuration.

Alternative Implementation 21

The dispenser assembly of any one of alternative implementations 18 to 20, wherein the medical device housed within the lubricious medical tube is a guide wire for use in a cardiovascular surgical procedure.

Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A medical tube formed from a blended material, comprising:
   at least about ninety-five percent organic polymer resin; and
   0.5 percent to three percent lubricity enhancing additive blended with the organic polymer resin to form the blended material, the lubricity enhancing additive being siloxane,
   wherein the blended material is extruded into the medical tube such that the medical tube has a substantially tubular configuration with an inner surface and an outer surface.

2. The medical tube of claim 1, wherein the organic polymer resin is high-density polyethylene.

3. The medical tube of claim 1, wherein the blended material further includes Franklinite.

4. The medical tube of claim 1, wherein the inner surface of the medical tube is formed with a plurality of elongated protuberances arranged to extend substantially parallel to a length dimension of the medical tube.

5. The medical tube of claim 4, wherein the plurality of elongated protuberances are configured such that each of the protuberances is characterized by a raised apex, the raised apex being closer to an axis of substantial cylindrical symmetry of the lubricious medical tube than a depressed region located between adjacent ones of the plurality of elongated protuberances.

6. The medical tube of claim 5, wherein the plurality of elongated protuberances are configured such that a medical guide wire inserted in the medical tube contacts at least a portion of one or more of the plurality of elongated protuberances, including the raised apexes, without contacting at least a portion of the inner surface between adjacent ones of the plurality of protuberances.

7. The medical tube of claim 4, wherein the plurality of elongated protuberances are substantially evenly spaced about the inner surface of the medical tube.

8. The medical tube of claim 1, wherein the inner surface of the medical tube is sufficiently lubricious to allow insertion or withdrawal of a guide wire into the medical tube while the medical tube is maintained in a coiled configuration.

9. The medical tube of claim 1, further comprising a medical device housed within the medical tube.

10. The medical tube of claim 9, wherein the medical device housed within the medical tube is a guide wire for use in a cardiovascular surgical procedure.

11. The medical tube of claim 9, wherein the medical device housed within the medical tube is a catheter.

12. The medical tube of claim 1, wherein the inner surface of the medical tube is smooth.

13. The medical tube of claim 1, wherein the lubricity enhancing additive has a melt flow index between about seven grams per ten minutes and about thirteen grams per ten minutes.

14. The medical tube of claim 1, wherein the lubricity enhancing additive has a bulk density between about thirty pounds per cubic foot and about thirty-five pounds per cubic foot.

15. The medical tube of claim 1, wherein the lubricity enhancing additive has a moisture content less than about one-half of a percent.

16. The medical tube of claim 1, wherein an outer diameter of the medical tube is between 0.152 inches and 0.300 inches and an inner diameter of the medical tube is between 0.100 inches and 0.250 inches.

17. A method of preparing a medical tube comprising:
blending an organic polymer resin with a lubricity enhancing additive to create a blended material, the blended material including at least about ninety-five percent organic polymer resin and 0.5 percent to three percent lubricity enhancing additive, the lubricity enhancing additive being siloxane and the organic polymer resin being high-density polyethylene;
controlling the temperature or pressure of the blended material so as to achieve a viscosity of the blended material suitable for extrusion;
extruding the blended material through a die, thereby forming a substantially tubular structure with an inner surface and an outer surface;
permitting the extruded tubular structure to cool for a predetermined amount of time; and
cutting the cooled extruded tubular structure, thereby forming the medical tube.

18. The method of claim 17, wherein the temperature is controlled to be between approximately 350 degrees and approximately 450 degrees.

* * * * *